(12) United States Patent
Richard (10) Patent No.: US 7,517,914 B2
(45) Date of Patent: Apr. 14, 2009

(54) CONTROLLED DEGRADATION MATERIALS FOR THERAPEUTIC AGENT DELIVERY

(75) Inventor: Robert E. Richard, Wrentham, MA (US)

(73) Assignee: Boston ScientificScimed, Inc., Maple Grove, MN (US)

( * ) Notice: Subject to any disclaimer, the term of this patent is extended or adjusted under 35 U.S.C. 154(b) by 666 days.

(21) Appl. No.: 11/098,729

(22) Filed: Apr. 4, 2005

(65) Prior Publication Data

US 2006/0222681 A1 Oct. 5, 2006

(51) Int. Cl.
*A61K 47/00* (2006.01)
*A61K 47/30* (2006.01)
*A61K 47/32* (2006.01)

(52) U.S. Cl. ............... 514/772.1; 514/772.3; 514/772.4; 514/772.6

(58) Field of Classification Search ............... 514/772.1, 514/772.3, 772.4, 772.6
See application file for complete search history.

(56) References Cited

U.S. PATENT DOCUMENTS

| | | | |
|---|---|---|---|
| 4,861,830 A * | 8/1989 | Ward, Jr. .................. 525/92 A |
| 5,410,016 A | 4/1995 | Hubbell et al. .............. 528/354 |
| 5,733,925 A | 3/1998 | Kunz et al. ................. 514/449 |
| 5,739,122 A | 4/1998 | Schehlmann et al. .......... 514/59 |
| 5,798,115 A * | 8/1998 | Santerre et al. ............. 424/423 |
| 6,545,097 B2 | 4/2003 | Pinchuk et al. ............. 525/240 |
| 6,641,833 B2 | 11/2003 | Dang |
| 2001/0016624 A1 | 8/2001 | Harris et al. ................ 525/54.1 |
| 2002/0150622 A1* | 10/2002 | Philbrook et al. ........... 424/486 |
| 2003/0153971 A1 | 8/2003 | Chandrasekaran ......... 623/1.15 |
| 2003/0153972 A1 | 8/2003 | Helmus ...................... 623/1.15 |
| 2003/0195152 A1 | 10/2003 | Suarato et al. ................ 514/12 |
| 2003/0202955 A1 | 10/2003 | Harris ...................... 424/78.17 |
| 2003/0211158 A1 | 11/2003 | Frechet et al. .............. 424/486 |
| 2003/0235603 A1 | 12/2003 | Schwarz et al. ............. 424/426 |
| 2003/0236513 A1* | 12/2003 | Schwarz et al. .......... 604/890.1 |
| 2004/0013637 A1 | 1/2004 | Bentley et al. ........... 424/78.17 |
| 2004/0076602 A1 | 4/2004 | Harris ..................... 424/78.38 |
| 2004/0106987 A1 | 6/2004 | Palasis et al. .............. 623/1.42 |
| 2004/0175406 A1 | 9/2004 | Schwarz ..................... 424/423 |

FOREIGN PATENT DOCUMENTS

WO WO 00/71180 A1 11/2000
WO WO 03/070805 A1 8/2003

OTHER PUBLICATIONS

Pyun, Jeffrey et al., "Synthesis of Nanocomposite Organic/Inorganic Hybrid Materials Using Controlled/"Living" Radical Polymerization," *Chem. Mater.*, 13:3436-3448 (2001).

* cited by examiner

*Primary Examiner*—Raymond J Henley, III
(74) *Attorney, Agent, or Firm*—Mayer & Williams PC; David B. Bonham (57) ABSTRACT

According to an aspect of the present invention, polymeric release regions are provided, which contain one or more partially biodegradable progenitor polymers and which control the release of one or more therapeutic agents disposed beneath or within the same. The progenitor polymers within the release regions are composed of a plurality of biostable polymer portions (which may be the same or different from one another) linked via one or more biodegradable linkages. Upon implantation or insertion into the body, the linkages degrade, cleaving the progenitor polymers into two or more biostable polymers of reduced molecular weight (relative to the molecular weight of the progenitor polymers). As a consequence of this reduction in molecular weight, the release characteristics of the release regions change over time.

22 Claims, 1 Drawing Sheet

CONTROLLED DEGRADATION MATERIALS FOR THERAPEUTIC AGENT DELIVERY

FIELD OF THE INVENTION

The present invention relates to therapeutic medical articles, including implantable or insertable medical devices, which contain polymer regions for release of therapeutic agents.

BACKGROUND OF THE INVENTION

The in vivo delivery of biologically active agents within the body of a patient is common in the practice of modern medicine. In vivo delivery of biologically active agents is often implemented using medical devices that may be temporarily or permanently placed at a target site within the body. These medical devices can be maintained, as required, at their target sites for short or prolonged periods of time, delivering biologically active agents at the target site.

For example, numerous polymer-based medical devices have been developed for the delivery of therapeutic agents to the body. Examples include drug eluting coronary stents, which are commercially available from Boston Scientific Corp. (TAXUS), Johnson & Johnson (CYPHER), and others.

In accordance with typical delivery strategies, a therapeutic agent is provided within or beneath a biostable or biodisintegrable polymeric layer that is associated with a medical device. Once the medical device is placed at the desired location on or within a patient, the therapeutic agent is released from the medical device with a profile that is dependent, for example, upon the loading of the therapeutic agent and upon the nature of the polymeric layer.

Controlling the rate of therapeutic agent release and the overall dose are key parameters for proper treatment in many cases. Selection of the polymeric layer will have a great impact on these parameters. Hence, the ability to tailor the polymeric constituents within the layer is of great interest.

SUMMARY OF THE INVENTION

According to an aspect of the present invention, polymeric release regions are provided, which contain one or more partially biodegradable progenitor polymers and which control the release of one or more therapeutic agents disposed beneath or within the same. The progenitor polymers within the release regions are composed of a plurality of biostable polymer portions (which may be the same or different from one another) linked via one or more biodegradable linkages. Upon implantation or insertion into the body, the linkages degrade, cleaving the progenitor polymers into two or more biostable polymers of reduced molecular weight (relative to the molecular weight of the progenitor polymers). As a consequence of this reduction in molecular weight, the release characteristics of the release regions change over time.

An advantage of the present invention is that polymeric release regions may be formed which provide at least two environments for therapeutic agent release—one prior to cleavage of the biodegradable linkages and another subsequent to cleavage of the biodegradable linkages.

Another advantage of the present invention is that polymeric release regions may be formed which are capable of releasing two or more therapeutic agents (e.g., a low molecular weight therapeutic agent and a high molecular weight therapeutic agent) at substantially different times, due to the changes that occur in the release regions subsequent to cleavage of the biodegradable linkages.

These and other embodiments and advantages of the present invention will become immediately apparent to those of ordinary skill in the art upon review of the Detailed Description and claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention. The scope of the invention is defined by the claims.

In one aspect, the present invention provides polymeric release regions, which control the release of therapeutic agents disposed beneath or within the same. These polymeric release regions contain one or more polymers, referred to herein as "progenitor polymers," which contain a plurality of (e.g., 2, 3, 4, 5, 6, 7, 8, 9, 10, or more) biostable polymer portions linked via one or more biodegradable linkages. Upon implantation or insertion into the body, the biodegradable linkages degrade, cleaving the progenitor polymers into two or more biostable polymers of reduced molecular weight (relative to the molecular weight of the progenitor polymers). As a consequence of this reduction in molecular weight, the release characteristics of the release regions evolve over time.

Figure 1:
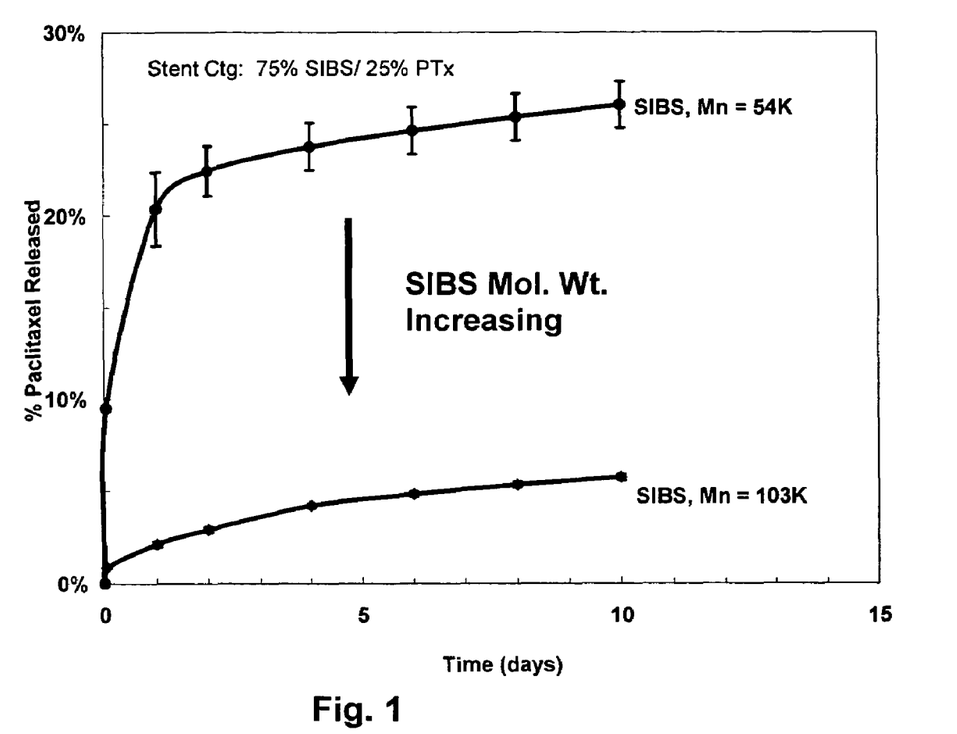
FIG. 1 illustrates kinetic drug release from stent coatings containing 25 wt % paclitaxel and 75 wt % polystyrene-polyisobutylene-polystyrene (SIBS) triblock copolymers of various molecular weights.

By way of background, it is known that the drug release profile associated with a given polymer will vary with molecular weight. For example, FIG. 1 illustrates kinetic drug release from stent coatings containing 25 wt % paclitaxel and 75 wt % polystyrene-polyisobutylene-polystyrene (SIBS) triblock copolymers of two molecular weights. As can be seen from this figure, as the molecular weight of the SIBS copolymer decreases, both the rate and the cumulative release of the paclitaxel increase.

Based on analogous principles, because the molecular weights of the polymers within the release regions of the present invention decrease upon implantation or insertion, the tendency of the release regions to release a given therapeutic agent may increase over time. Consequently, polymeric release regions may be provided which have at least two environments for therapeutic agent release—one prior to cleavage of the biodegradable linkages and another subsequent to cleavage of the biodegradable linkages.

Additionally, polymeric release regions may be provided in accordance with the present invention, which release multiple therapeutic agents at substantially different times, due to the relative mobilities of the therapeutic agents within the release region before and after cleavage of the biodegradable linkages. For example, prior to linkage degradation, a lower molecular weight therapeutic agent may be freely and substantially released from the polymeric release region, whereas a higher molecular weight therapeutic agent may be released very slowly or even trapped within the release region. However, subsequent to linkage breakdown, the rate of release of the higher molecular weight therapeutic agent is increased.

Regardless of whether single or multiple therapeutic agents are present, the release rate can be tailored by including one or more types of biodegradable linkages within the release region. In addition, two or more types of biodegradable linkages may be provided within the release region, each having differing degradation kinetics. These biodegradable linkages may be present within a single progenitor polymer, or multiple progenitor polymers may be present, each with its own unique biodegradable linkages, and so forth As used herein "polymeric release regions" are regions that comprise polymers and control the release of one or more therapeutic agents, typically comprising at least 50 wt % to 75 wt % to 90 wt % to 95 wt % or even more polymers.

Polymeric release regions in accordance with the present invention include a variety of therapeutic articles, including pharmaceutical compositions and medical devices.

Examples of pharmaceutical compositions include compositions for oral, nasal, rectal, vaginal, intravenous, intraarterial, intramuscular, subcutaneous or peritoneal administration, including tablets, pills, capsules, suppositories, powders, sprays, aerosols, solutions, suspensions, emulsions, and so forth.

Examples of medical devices include implantable or insertable medical devices, for example, catheters (e.g., renal or vascular catheters such as balloon catheters), guide wires, balloons, filters (e.g., vena cava filters), stents (including coronary vascular stents, peripheral vascular stents, cerebral, urethral, ureteral, biliary, tracheal, gastrointestinal and esophageal stents), stent grafts, vascular grafts, vascular access ports, embolization devices including cerebral aneurysm filler coils (including Guglilmi detachable coils and metal coils), myocardial plugs, patches, pacemakers and pacemaker leads, left ventricular assist hearts and pumps, total artificial hearts, heart valves, vascular valves, biopsy devices, and any coated substrate (which can comprise, for example, glass, metal, polymer, ceramic and combinations thereof) that is implanted or inserted into the body and from which therapeutic agent is released. Examples of medical devices further include patches for delivery of therapeutic agent to intact skin and broken skin (including wounds); sutures, suture anchors, anastomosis clips and rings, tissue staples and ligating clips at surgical sites; cannulae, metal wire ligatures, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; tissue bulking devices, and tissue engineering scaffolds for cartilage, bone, skin and other in vivo tissue regeneration.

The medical devices of the present invention include implantable and insertable medical devices that are used for diagnosis, for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects (also referred to as "patients") are vertebrate subjects, more preferably mammalian subjects and more preferably human subjects.

Specific examples of medical devices for use in conjunction with the present invention include vascular stents, such as coronary stents and cerebral stents, which deliver a therapeutic agent into the vasculature for the treatment of restenosis.

In some embodiments, the polymeric release regions of the present invention correspond to an entire medical article. In other embodiments, the polymeric release regions correspond or to one or more portions of a medical article. For instance, the polymeric release regions can be in the form of one or more fibers which are incorporated into a medical article, in the form of one or more polymeric layers formed over all or only a portion of an underlying medical article substrate, and so forth. Layers can be provided over an underlying substrate at a variety of locations, and in a variety of shapes, and they can be formed from a variety of polymeric materials. Materials for use as underlying medical article substrates include ceramic, metallic and polymeric substrates. The substrate material can also be a carbon- or silicon-based material. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

Release regions in accordance with the present invention include carrier regions and barrier regions. By "carrier region" is meant a release region which further comprises a therapeutic agent and from which the therapeutic agent is released. For example, in some embodiments, the carrier region constitutes the entirety of the medical article (e.g., provided in the form of a stent body). In other embodiments, the carrier region corresponds to only a portion of the article (e.g., a coating overlying a medical article substrate such as a stent body). By "barrier region" is meant a region which is disposed between a source of therapeutic agent and a site of intended release, and which controls the rate at which therapeutic agent is released. For example, in some embodiments, the medical article contains a barrier region that surrounds a source of therapeutic agent. In some embodiments, the barrier region is disposed over a source of therapeutic agent, which is in turn disposed over all or a portion of a medical article substrate.

As previously indicated, the polymeric release regions of the present invention contain progenitor polymers which in turn contain a plurality of biostable polymer portions that are linked together via one or more biodegradable linkages.

As used herein, "polymers" and "polymer portions" are entire molecules and portions of molecules, respectively, which contain one or more chains, each containing multiple copies of the same or differing constitutional units, commonly referred to as monomers. An example of a common polymer chain is polystyrene where n is an integer of 2 or more, typically an integer of 10 or more, more typically on the order of 10's, 100's, 1000's or even more, in which the chain contains styrene monomers:

(i.e., the chain originates from, or has the appearance of originating from, the polymerization of styrene monomers, in this case, the addition polymerization of styrene monomers).

A "chain" is an unbranched monomer grouping. Polymers and polymer portions, however, can have a variety of architectures, including linear, branched and cyclic architectures. Branched architectures include star-shaped architectures (e.g., architectures in which three or more chains emanate from a single branch point), comb architectures (e.g., architectures having a main chain and a plurality of side chains) and dendritic architectures (e.g., arborescent and hyperbranched polymers), among others.

The plurality of polymer portions making up the progenitor polymers can be homopolymer portions, in which all monomers are the same, or copolymer portions, in which two or more differing monomers maybe present in any distribution, including, for example, random, statistical, gradient periodic, and block distributions.

Polymer portions making up the progenitor polymers can be the same or different. In saying that two polymer portions are "different," one or more of the following is meant: (a) one polymer portion contains a monomer constituent that is not found in the other polymer portion, (b) the two polymer portions have different architectures (e.g., linear vs. branched) and (c) for copolymer portions, one polymer portion has a comonomer distribution that is different from the other (e.g., one portion is random whereas the other is alternating, and so forth). Polymer portions that vary only in molecular weight are considered to be the same for purposes of the present invention.

By "biostable polymer portion" is meant a polymer portion that does not undergo substantial degradation (i.e., bond cleavage) during the time over which the medical article is designed to reside in the body (which can be on the order of hours, days, weeks, months or even years), but rather remains substantially associated with the medical article during this time.

Conversely, by "biodegradable linkage" is meant a linkage that undergoes bond cleavage during the time over which the medical article is designed to reside in the body.

The biodegradable linkages that can be used in the progenitor polymers of the invention include any known linkages that will cleave in the in vivo environment, during the time over which the medical article is designed to reside in the body, such that the progenitor polymer is cleaved into two or more polymers of lower molecular weight (which correspond to the polymer portions making up the progenitor polymer).

Biodegradable linkages can be selected, for example, from the following known biodegradable linkages, among others: carboxylate ester linkages, phosphate ester linkages, imine linkages, hydrazone linkages, acetal linkages, orthoester linkages, carbamate linkages, carbonate linkages, amide linkages, thiol based linkages such as thioester linkages, disulfide linkages, anhydride linkages, urea linkages, oligonucleotide linkages, peptide linkages, linkage by Schiff base crosslink, p-nitrophenyl chloroformate linkages, carbonyldiimidazole linkages, N,N'-disuccinimidyl carbonate linkages, and so forth. Specific examples of linkages are linkages that contain one or more constitutional units corresponding to known biodegradable polymers, including, for example, lactide units, glycolide units, trimethylene carbonate units, and so forth.

A wide array of polymer portions is commercially available, or can be synthesized, for use in forming the progenitor polymers of the present invention. For example, suitable polymer portions can be selected from the following: (a) homopolymer and copolymer portions consisting of or containing one or more acrylic acid monomers such as the following: acrylic acid and its salt forms (e.g., potassium acrylate and sodium acrylate); acrylic acid anhydride; acrylic acid esters including alkyl acrylates (e.g., methyl acrylate, ethyl acrylate, propyl acrylate, isopropyl acrylate, butyl acrylate, sec-butyl acrylate, isobutyl acrylate, tert-butyl acrylate, hexyl acrylate, cyclohexyl acrylate, isobornyl acrylate, 2-ethylhexyl acrylate, dodecyl acrylate and hexadecyl acrylate), arylalkyl acrylates (e.g., benzyl acrylate), alkoxyalkyl acrylates (e.g., 2-ethoxyethyl acrylate and 2-methoxyethyl acrylate), halo-alkyl acrylates (e.g., 2,2,2-trifluoroethyl acrylate) and cyano-alkyl acrylates (e.g., 2-cyanoethyl acrylate); acrylic acid amides (e.g., acrylamide, N-isopropylacrylamide and N,N dimethylacrylamide); and other acrylic-acid derivatives (e.g., acrylonitrile); (b) homopolymer and copolymer portions consisting of or containing one or more methacrylic acid based monomers such as the following: methacrylic acid and its salts (e.g., sodium methacrylate); methacrylic acid anhydride; methacrylic acid esters (methacrylates) including alkyl methacrylates (e.g., methyl methacrylate, ethyl methacrylate, isopropyl methacrylate, butyl methacrylate, isobutyl methacrylate, t-butyl methacrylate, hexyl methacrylate, cyclohexyl methacrylate, 2-ethylhexyl methacrylate, octyl methacrylate, dodecyl methacrylate, hexadecyl methacrylate, octadecyl methacrylate, aromatic methacrylates (e.g., phenyl methacrylate and benzyl methacrylate), hydroxyalkyl methacrylates (e.g., 2-hydroxyethyl methacrylate and 2-hydroxypropyl methacrylate), aminoalkyl methacrylates (e.g., diethylaminoethyl methacrylate and 2-tert-butyl-aminoethyl methacrylate), additional methacrylates (e.g., isobornyl methacrylate and trimethylsilyl methacrylate); and other methacrylic-acid derivatives (e.g., methacrylonitrile); (c) homopolymer and copolymer portions consisting of or containing one or more vinyl aromatic monomers (i.e., those having aromatic and vinyl moieties) such as the following: unsubstituted vinyl aromatics (e.g., styrene and 2-vinyl naphthalene); vinyl substituted aromatics (e.g., α-methyl styrene); and ring-substituted vinyl aromatics including ring-alkylated vinyl aromatics (e.g., 3-methylstyrene, 4-methylstyrene, 2,4-dimethylstyrene, 2,5-dimethylstyrene, 3,5-dimethylstyrene, 2,4,6-trimethylstyrene, and 4-tert-butylstyrene), ring-alkoxylated vinyl aromatics (e.g., 4-methoxystyrene and 4-ethoxystyrene), ring-halogenated vinyl aromatics (e.g., 2-chlorostyrene, 3-chlorostyrene, 4-chlorostyrene, 2,6-dichlorostyrene, 4-bromostyrene and 4-fluorostyrene) and ring-ester-substituted vinyl aromatics (e.g., 4-acetoxystyrene); (d) homopolymer and copolymer portions consisting of or containing one or more vinyl monomers (beyond the above vinyl aromatic monomers) such as the following: vinyl alcohol; vinyl esters (e.g., vinyl benzoate, vinyl 4-tert-butyl benzoate, vinyl cyclohexanoate, vinyl pivalate, vinyl trifluoroacetate and vinyl butyral); vinyl amines (e.g., 2-vinyl pyridine, 4-vinyl pyridine, and vinyl carbazole); vinyl halides (e.g., vinyl chloride and vinyl fluoride); alkyl vinyl ethers (e.g., methyl vinyl ether, ethyl vinyl ether, propyl vinyl ether, butyl vinyl ether, isobutyl vinyl ether, 2-ethylhexyl vinyl ether, dodecyl vinyl ether, tert-butyl vinyl ether and cyclohexyl vinyl ether); and other vinyl compounds (e.g., 1-vinyl-2-pyrrolidone and vinyl ferrocene); (e) homopolymer and copolymer portions consisting of or containing one or more aromatic monomers (beyond the above vinyl aromatic monomers) such as acenaphthalene and indene; (f) homopolymer and copolymer portions consisting of or containing one or more cyclic ether monomers such as the following: tetrahydrofuran, trimethylene oxide, methyl glycidyl ether, butyl glycidyl ether, allyl glycidyl ether, epibromohydrin, epichlorohydrin, 1,2-epoxybutane, 1,2-epoxyoctane and 1,2-epoxydecane; (g) homopolymer and copolymer portions consisting of or containing one or more ester monomers (beyond those ester monomers listed above) such as ethylene malonate, vinyl acetate and vinyl propionate; (h) homopolymer and copolymer portions consisting of or containing one or more alkene monomers such as the following: unsubstituted alkene monomers (e.g., ethylene, propylene, isobutylene, 1-butene, trans-butadiene, 4-methyl pentene, 1-octene, 1-octadecene, and other α-olefins, as well as cis-isoprene and trans-isoprene) and halogenated alkene monomers (e.g., vinylidene chloride, vinylidene fluoride, cis-chlorobutadiene, trans-chlorobutadiene, and tetrafluoroethylene); and (i) homopolymer and copolymer portions consisting of or containing one or more organo-siloxane monomers such as dimethylsiloxane, diethylsiloxane, methylethylsiloxane, methylphenylsiloxane and diphenylsiloxane.

As will be appreciated by those of ordinary skill in the art, a wide range of polymer portions may be synthesized from the above and other monomers, according to a number of known polymerization methods, including anionic, cationic and radical polymerization methods, such as azobis(isobutyronitrile)- or peroxide-initiated polymerizations and controlled/"living" radical polymerizations such as metal-catalyzed atom transfer radical polymerization (ATRP), stable free-radical polymerization (SFRP), nitroxide-mediated processes (NMP), and degenerative transfer (e.g., reversible addition-fragmentation chain transfer (RAFT)) processes, among others. These methods are well-detailed in the literature and are described, for example, in an article by Pyun and Matyjaszewski, "Synthesis of Nanocomposite Organic/Inorganic Hybrid Materials Using Controlled/"Living" Radical Polymerization," *Chem. Mater.*, 13:3436-3448 (2001), the contents of which are incorporated by reference in its entirety.

As further examples, suitable polymer portions for use within the progenitor polymers of the present invention, which are not necessarily exclusive of the above examples, can be selected from the following: polyolefin portions such as polyethylenes, polypropylenes, and polybutylenes; polyolefin copolymer portions, e.g., ethylenic copolymer portions such as ethylene vinyl acetate (EVA) copolymer portions; ethylene-methacrylic acid copolymer portions and ethylene-acrylic acid copolymer portions where some of the acid groups can be neutralized, e.g., with zinc or sodium ions (commonly known as ionomers); vinyl aromatic polymer and copolymer portions such as styrene-ethylene-butylene copolymer portions (e.g., a polystyrene-polyethylene/butylene-polystyrene (SEBS) copolymer portions, available as Kraton® G series polymers); styrene-isobutylene copolymer portions (e.g., polystyrene-polyisobutylene-polystyrene (SIBS) copolymer portions such as those disclosed in U.S. Pat. No. 6,545,097 to Pinchuk); butadiene-styrene copolymer portions, and styrene-maleic acid (SMA) copolymer portions (e.g., random copolymer portions of styrene and maleic anhydride, such as those available from Nova Chemical, and alternating copolymer portions of styrene and maleic anhydride, such as those available from Scientific Polymer Products, Inc.); polyacetal portions; chloropolymer portions such as polyvinyl chloride (PVC) portions; fluoropolymer portions such as polytetrafluoroethylene (PTFE) portions; polyester portions such as polyethyleneterephthalate (PET) portions; polyester-ether portions; polyamide portions such as nylon 6 and nylon 6,6 portions; polyether portions; polyamide ether portions including polyether-polyaminde portions; silicone portions; polycarbonate portions; thermoplastic polyurethane portions (TPU); and elastomeric polyurethane portions (including copolymer portions that are polyether based, polyester based, polycarbonate based, aliphatic based, aromatic based and mixtures thereof; examples of commercially available polyurethane copolymer portions include Carbothane®, Tecoflex®, Tecothane®, Tecophilic®, Tecoplast®, Pellethane®, Chronothane® and Chronoflex®).

In certain embodiments, polymer portions for use in the present invention are selected, at least in part, based on their associated $T_g$'s (glass transition temperatures). A "low $T_g$ polymer portion" is a polymer portion that displays at least one glass transition temperature that is below ambient temperature, more typically below about 25° C., below about 0° C., below about −25° C., or even below about −50° C. $T_g$ can be measured by any of a number of techniques including differential scanning calorimetry (DSC), dynamic mechanical analysis (DMA), or dielectric analysis (DEA). "Ambient temperature" is typically 25° C.-45° C., more typically body temperature (e.g., 35° C.-40° C.). An elevated or "high $T_g$ polymer portion" is a polymer portion that displays at least one glass transition temperature that is above ambient temperature, more typically above 50° C., above 60° C., above 70° C., above 80° C., above 90° C. or even above 100° C. As a general rule, polymer portions displaying low $T_g$'s will be soft and elastic at ambient temperature, whereas polymer portions displaying high $T_g$'s will be rigid at ambient temperature.

Polymers displaying both high and low $T_g$'s are known to possess many interesting physical properties. As a specific example, polyisobutylene-polystyrene polymers, for example, polystyrene-polyisobutylene-polystyrene (SIBS), described in U.S. Pat. No. 6,545,097 to Pinchuk et al., which is hereby incorporated by reference in its entirety, have proven valuable as release polymers in implantable or insertable drug-releasing medical devices. These polymers are particularly useful for medical device applications because of their excellent strength as well as their excellent biostability and biocompatibility, particularly within the vasculature. For example, these polymers exhibit high tensile strength, which frequently ranges from 2,000 to 4,000 psi or more, and resist cracking and other forms of degradation under typical in vivo conditions. Biocompatibility, including vascular compatibility, of these materials has been demonstrated by their tendency to provoke minimal adverse tissue reactions (e.g., as measured by reduced macrophage activity). In addition, these polymers are generally hemocompatible as demonstrated by their ability to minimize thrombotic occlusion of small vessels when applied as a coating on coronary stents.

A few specific embodiments of polymers for use in conjunction with the invention follow. One factor common to each of these embodiments is that cleavage of the biodegradable linkages leads to polymers of reduced molecular weight.

For instance, in some embodiments, progenitor polymers are provided in which biodegradable linkages are situated between adjacent homopolymer portions having the same monomer content. Upon breakdown, the resulting homopolymers have essentially the same composition as the progenitor polymer, only having reduced molecular weights (they are thus considered to be the "same" for purposes of the present invention). Examples of such polymers include homopolymers that degrade into two smaller polymers (e.g., polyA-d-polyA, where "d" designates a biodegradable linkage), three smaller polymers (e.g., polyA-d-polyA-d-polyA), or more (e.g., polyA-d-polyA-d-polyA-d-polyA, polyA-d-polyA-d-polyA-d-polyA-d-polyA, and so forth), where A is a monomer that can be selected, for example, from those described above (e.g., an acrylate, methacrylate, vinyl aromatic, vinyl alcohol, vinyl ester, vinyl amine, vinyl halide, vinyl ether, alkene, or dialkylsiloxane monomer).

In other embodiments, progenitor polymers are provided in which biodegradable linkages are situated between adjacent copolymer portions which have substantially the same monomer content and distribution. Upon breakdown, the resulting copolymers have essentially the same composition as the progenitor polymer, only having reduced molecular weights. Examples of such polymers include poly(B-r-C)-d-poly(B-r-C), poly(B-r-C)-d-poly(B-r-C)-d-poly(B-r-C), poly(B-alt-C)-d-poly(B-alt-C), poly(B-alt-C)-d-poly(B -alt-C)-d-poly(B-alt-C), polyB-polyC-d-polyB-polyC, polyB-polyC-d-polyB-polyC-d-polyB-polyC, and so forth, where alt and r denote alternating and random monomer arrangements, and where B and C are different monomers, which can be selected, for example, from those monomers described above (e.g., acrylate, methacrylate, vinyl aromatic, vinyl alcohol, vinyl ester, vinyl amine, vinyl halide, vinyl ether, alkene, and dialkylsiloxane monomers).

In other embodiments, progenitor polymers are provided in which biodegradable linkages are situated between adjacent homopolymer or copolymer portions which have different monomer content, architecture and/or (for copolymers) monomer distribution. Specific examples include polyB-d-polyC and polyB-d-polyC-d-polyB progenitor copolymers (which break down into polyB and polyC homopolymers), poly(B-r-C)-d-poly(B) (which breaks down into a polyB homopolymer and a poly(B-r-C) copolymer), poly(B-r-C)-d-poly(B-alt-C) (which breaks down into poly(B-r-C) and poly (B-alt-C) copolymers), polyB-d-polyB-polyC-polyB-d-polyB progenitor copolymer (which breaks down into polyB homopolymer and polyB-polyC-polyB triblock copolymer), and so forth.

Most of the above examples are directed to linear progenitor polymers. In other embodiments, however, cyclic and branched progenitor polymers are employed. As a specific example, in some embodiments, comb progenitor polymers are provided in which multiple polymer portions of a first type are linked via biodegradable linkages to another polymer portion of the same or differing type, along its length. For example multiple polyB portions may be provided along the length of a polyC portion. As another example, radial arm progenitor polymers are provided in which multiple polymer portions are linked via biodegradable linkages to a multiarm central block. Examples include, X(polyB-d-polyC)$_n$ where X is a hub species (e.g., an initiator species) and n is an integer of 3 or more.

Using the above and similar principles, it will become readily apparent to those of ordinary skill in the art that a wide variety of polymer portions can be linked to form a vast array of progenitor polymers.

As indicated above, various therapeutic agents can be disposed on or within the polymeric release regions of the present invention.

"Drugs," "therapeutic agents," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of portioning smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (O) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta -portioners, (u) bARKct inhibitors, (v) phospholamban inhibitors, and (w) Serca 2 gene/protein.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-portioners, bARKct inhibitors, phospholamban inhibitors, and Serca 2 gene/protein among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet -derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated viruses, retroviruses, alpha viruses (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage; or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel portioners including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate; thrombin inhibitors such as hirudin, hirulog, PPACK(D-phe-L-propyl-L-arg-chloromethylketone) and argatroban; FXa inhibitors such as antistatin and TAP (tick anticoagulant peptide); Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins; PDGF receptor antagonists such as trapidil; IGF pathway agents including somatostatin analogs such as angiopeptin and ocreotide; TGF-β pathway agents such as polyanionic agents (heparin, fucoidin), decorin, and TGF-β, antibodies; EGF pathway agents such as EGF antibodies, receptor antagonists and chimeric fusion proteins; TNF-α pathway agents such as thalidomide and analogs thereof; Thromboxane A2 (TXA2) pathway modulators such as sulotroban, vapiprost, dazoxiben and ridogrel; as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

A wide range of therapeutic agent loadings can be used in conjunction with the polymeric release regions of the present invention, with the therapeutically effective amount being readily determined by those of ordinary skill in the art and ultimately depending, for example, upon the condition to be treated, the age, sex and condition of the patient, the nature of the therapeutic agent, the nature of the polymeric release region(s), the nature of the medical article, and so forth.

The release profiles associated with the medical articles of the present invention can not only be modified by changing the polymeric constituents (including the progenitor polymers) within the release regions of the same, but also by changing the size, number or position of the polymeric release regions within the device. For example, the release profile of polymeric carrier and barrier layers in accordance with the presenting invention can be modified by varying the thickness or surface areas of the same. Moreover, multiple polymeric release regions can be employed to modify the release profile. For example, multiple carrier or barrier layers of the invention, either having the same or different content (e.g., different polymeric and/or therapeutic agent content), can be stacked on top of one another, can be positioned laterally relative to one another, and so forth.

Numerous techniques are available for forming polymeric release regions in accordance with the present invention.

For example, where the polymeric release regions are formed from one or more polymers having thermoplastic characteristics and where the materials making up the release regions (including the linkages within the progenitor polymers) are stable under thermoplastic processing conditions, then a variety of thermoplastic processing techniques can be used to form the polymeric release regions, including compression molding, injection molding, blow molding, spinning, vacuum forming and calendaring, as well as extrusion into sheets, fibers, rods, tubes and other cross-sectional profiles of various lengths. Using these and other thermoplastic processing techniques, entire medical articles of portions thereof can be made.

As another example, where the polymers forming the polymeric release regions (including the progenitor polymers) are solvent-soluble, and where the materials making up the release regions (including the linkages within the progenitor polymers) are stable under solvent processing conditions, then a variety of solvent-based techniques can be used to form the polymeric release regions of the present invention, including solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a polymer melt (where thermoplastic processing is employed) or polymer containing solution (where solvent-based processing is employed) is applied to a substrate to form a polymeric release region. For example, the substrate can correspond to all or a portion of an implantable or insertable medical device to which a polymeric release region is applied. The substrate can also be, for example, a template, such as a mold, from which the polymeric release region is removed after solidification. In other embodiments, for example, extrusion and co-extrusion techniques, one or more polymeric release regions are formed without the aid of a substrate.

In a more specific example, an entire stent body is extruded. In another, a polymer release layer is co-extruded along with and underlying stent body. In another, a polymeric layer is provided on an underlying stent body by spraying or extruding a coating layer onto a pre-existing stent body. In yet another more specific example, a stent is cast in a mold.

If it is desired to provide one or more therapeutic agents and/or any other optional agents in the polymeric release region, and so long as these agents are stable under processing conditions, then they can be provided within the polymer melt or polymer containing solution and co-processed along with the polymer(s).

Alternatively, therapeutic and/or other optional agents may be introduced subsequent to the formation of the polymeric release region. For instance, in some embodiments, the therapeutic and/or other optional agents are dissolved or dispersed within a solvent, and the resulting solution contacted with a previously formed polymeric release region (e.g., using one or more of the application techniques described above, such as dipping, spraying, etc.).

As noted above, barrier layers are formed over a therapeutic-agent-containing region in some embodiments of the invention. In these embodiments, a polymeric barrier region can be formed over a therapeutic-agent-containing region, for example, using one of the solvent-based or thermoplastic techniques described above. Alternatively, a previously formed polymeric release region can be applied over (e.g., by adhesion) a therapeutic agent containing region.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A therapeutic article comprising (a) a polymeric release region, said polymeric release region comprising a progenitor polymer that comprises a plurality of biostable polymer portions covalently linked to one another via one or more biodegradable linkages, wherein said biostable polymer portions comprise a biostable homopolymer or copolymer portion having a glass transition temperature below body temperature and a biostable homopolymer or copolymer portion having a glass transition temperature above body temperature, and (b) a therapeutic agent disposed beneath or within said polymeric release region.

2. The therapeutic article of claim 1 wherein said one or more biodegradable linkages comprise a linkage selected from a glycolide linkage, a lactide linkage, a trimethylene carbonate linkage, and combinations of the same.

3. The therapeutic article of claim 1 wherein said progenitor polymer comprises more than two biostable polymer portions.

4. The therapeutic article of claim 1 wherein said plurality of biostable polymer portions are linear.

5. The therapeutic article of claim 1 wherein said homopolymer or copolymer portion having a glass transition temperature below body temperature comprises a monomer selected from acrylic monomers, methacrylic monomers, vinyl ether monomers, cyclic ether monomers, ester monomers, alkene monomers, halogenated alkene monomers, siloxane monomers and combinations thercot and wherein said homopolymer or copolymer portion having a glass transition temperature above body temperature comprises a monomer selected from vinyl monomers, aromatic monomers, vinyl aromatic monomers, acrylic monomers, methacrylic monomers, and combinations thereof.

6. The therapeutic article of claim 1 wherein said progenitor polymer comprises a linear or star shaped biostable polymer portion having two or more arms and additional biostable polymer portions which are linked to said arms via said biodegradable linkages.

7. The therapeutic article of claim 1 wherein said progenitor polymer comprises a branched biostable polymer portion and additional biostable polymer portions which are linked to branches of said branched polymer portion via biodegradable linkages.

8. The therapeutic article of claim 1 wherein said progenitor polymer comprises one linear biostable polymer portion and additional biostable polymer portions linked along the backbone of said linear biostable polymer portion via biodegradable linkages.

9. The therapeutic article of claim 1 wherein said progenitor polymer comprises alternating polymer portions which differ from one another and are linked via biodegradable linkages.

10. The therapeutic article of claim 1 wherein the therapeutic article is adapted for oral, nasal, rectal, vaginal, intravenous, intraarterial, intramuscular, subcutaneous or peritoneal administration.

11. The therapeutic article of claim 1 wherein the therapeutic article is a medical device, at least a portion of which is configured for implantation or insertion into a subject.

12. The therapeutic article of claim 11 wherein said therapeutic agent is disposed within said polymer release region.

13. The therapeutic article of claim 11 wherein said polymer release region is disposed over said therapeutic agent.

14. The therapeutic article of claim 11 wherein said polymeric release region constitutes the entirety of the medical device.

15. The therapeutic article of claim 11 wherein said polymeric release region constitutes a portion of the medical device.

16. The therapeutic article of claim 11 wherein said polymeric release region is disposed over a medical device substrate.

17. The therapeutic article of claim 16 wherein said polymeric release region is a polymeric release layer.

18. The therapeutic article of claim 1 wherein said one or more biodegradable linkages comprise a linkage selected from polyester linkages, polycarbonate linkages, polyorthoester linkages, polyanhydride linkages, polyamide linkages, polysaccharide linkages, and combinations of the same.

19. The therapeutic article of claim 1 wherein said homopolynier or copolymer portion having a glass transition temperature below body temperature comprises a monomer selected from alkyl acrylate monomers, alkyl methacrylate monomers, alkene monomers, halogenated alkene monomers, siloxane monomers and combinations thereof; and wherein said homopolymer or copolymer portion having a glass transition temperature above body temperature comprises a monomer selected from vinyl aromatic monomers, alkyl acrylate monomers, alkyl methacrylate monomers, and combinations thereof.

20. The therapeutic article of claim 1 wherein said homopolymer or copollymer portion having a glass transition temperature below body temperature comprises a monomer selected from butyl acrytate, isobutylene, dimethylsiloxane, and combinations thereof, and wherein said homopolymer or copolymer portion having a glass transition temperature above body temperature comprises a monomer selected from styrene, methyl methacrylate, and combinations thereof.

21. The therapeutic article of claim 1 wherein said homopolymer or copolymer portion having a glass transition temperature below body temperature comprises isobutylene and wherein said homopolymer or copolynaer portion having a glass transition temperature above body temperature comprises styrene.

22. The therapeutic article of claim 1 wherein the progenitor polymer and the therapeutic agent are distinct entities.

* * * * *

UNITED STATES PATENT AND TRADEMARK OFFICE
CERTIFICATE OF CORRECTION

PATENT NO. : 7,517,914 B2
APPLICATION NO. : 11/098729
DATED : April 14, 2009
INVENTOR(S) : Robert E. Richard It is certified that error appears in the above-identified patent and that said Letters Patent is hereby corrected as shown below:

Col. 1, line 13, before "delivery", change "in vivo" to --*in vivo*--.

Col. 1, line 15, before "delivery", change "in vivo" to --*in vivo*--.

Col. 3, line 6, after "forth", insert --.--.

Col. 3, line 48, before "tissue", change "in vivo" to --*in vivo*--.

Col. 4, line 8, before "to", delete "or".

Col. 5, line 25, after "monomers", change "maybe" to --may be--.

Col. 5, line 53, before "environment", change "in vivo" to --*in vivo*--.

Col. 8, line 48, after "typical", change "in vivo" to --*in vivo*--.

Col. 9, line 16, after "include", change "poly(B-r-C)-d-poly(B-r-" to --poly(B-*r*-C)-d-poly(B-*r*- --.

Col. 9, line 17, after "C)", change "poly(B-r-C)-d-poly(B-r-C)-d-poly(B-r-C)" to --poly(B-*r*-C)-d-poly(B-*r*-C)-d-poly(B-*r*-C)--.

Col. 9, line 18, before "poly(B-alt-C)-d-poly(B –alt-c)-d-poly" change "C)-d-poly(B-alt-C)" to --C)-d-poly(B-*alt*-C)--.

Col. 9, line 18, after "C)-d-poly(B-alt-C)", change "poly(B-alt-C)-d-poly(B –alt-C)-d-poly" to --poly(B-*alt*-C)-d-poly(B-*alt*-C)-d-poly--.

Col. 9, line 19, before "polyB-polyC-d-polyB-polyC", change "(B-alt-C)" to --(B-*alt*-C)--.

Col. 9, line 20, after "where", change "alt" to --*alt*-- and "r" to --*r*--.

UNITED STATES PATENT AND TRADEMARK OFFICE
CERTIFICATE OF CORRECTION

PATENT NO. : 7,517,914 B2
APPLICATION NO. : 11/098729
DATED : April 14, 2009
INVENTOR(S) : Robert E. Richard It is certified that error appears in the above-identified patent and that said Letters Patent is hereby corrected as shown below:

Col. 9, line 34, before "(which", change "poly(B-r-C)-d-poly(B)" to

--poly(B-*r*-C)-d-poly(B)--.

Col. 9, line 35, before "copolymer),", change "poly(B-r-C)" to

--poly(B-*r*-C)--.

Col. 9, line 35, after "copolymer),", change "poly(B-r-C)-d-" to

--poly(B-*r*-C)-d- --.

Col. 9, line 36, before "(which", change "poly(B-alt-C)" to

--poly(B-*alt*-C)--.

Col. 9, line 36, after "into", change "poly(B-r-C)" to --poly(B-*r*-C)--.

Col. 9, line 37, before "copolymers)", change "(B-alt-C)" to --(B-*alt*-C)--.

Col. 10, line 33, before "agents that interfere", change "(O)" to --(o)--.

Col. 10, line 59, after "factor,", change "platelet –derived" to

--platelet-derived--.

Col. 13, line 29, after "articles", change "of" to --or--.

Claim 5, Col. 14, line 50, after "combinations", change "thercot" to --thereof,--.

Claim 12, Col. 15, line 16, after "Said", change "polymer" to --polymeric--.

Claim 13, Col. 15, last word in line 17, after "said", change "polymer" to --polymeric--.

Claim 18, Col. 15, line 32, after "linkages", change "comprise" to --comprises--.

UNITED STATES PATENT AND TRADEMARK OFFICE
CERTIFICATE OF CORRECTION

PATENT NO. : 7,517,914 B2
APPLICATION NO. : 11/098729
DATED : April 14, 2009
INVENTOR(S) : Robert E. Richard It is certified that error appears in the above-identified patent and that said Letters Patent is hereby corrected as shown below:

Claim 19, Col. 16, line 5 before "or copolymer", change "homopolynier" to --homopolymer--.

Claim 20, Col. 16, line 16, before "portion", change "copollymer" to --copolymer--.

Claim 20, Col. 16, line 18, after "butyl", change "acrytate" to --acrylate--.

Claim 21, Col. 16, line 26, before "portion", change "copolynaer" to --copolymer--.

Signed and Sealed this

Nineteenth Day of May, 2009

JOHN DOLL
*Acting Director of the United States Patent and Trademark Office*